United States Patent [19]
Fletcher et al.

[11] 3,988,933
[45] Nov. 2, 1976

[54] FLUID MASS SENSOR FOR A ZERO GRAVITY ENVIRONMENT

[76] Inventors: James C. Fletcher, Administrator of the National Aeronautics and Space Administration with respect to an invention of; G. L. Fogal, Wayne, Pa.

[22] Filed: Nov. 7, 1974

[21] Appl. No.: 521,816

[52] U.S. Cl. .............................. 73/432 R; 177/1; 177/208
[51] Int. Cl.² .................... G01L 19/14; G01G/5/04
[58] Field of Search............ 177/1, 208; 73/194 M, 73/214, 432 R

[56] References Cited
UNITED STATES PATENTS
1,956,309   4/1934   Borden .............................. 73/214

Primary Examiner—George H. Miller, Jr.
Attorney, Agent, or Firm—Marvin J. Marnock; John R. Manning; Marvin F. Matthews

[57] ABSTRACT

Apparatus and method for determining the mass of a fluid comprising: a housing having an inlet and outlet for receiving and dumping the fluid, a rotary impeller within the housing for imparting centrifugal motion to the fluid and a pressure sensitive transducer attached to the housing to sense the rotating fluid pressure. In the method the fluid may be drawn into the housing by entrainment within a gas stream. The resulting mixture is then separated into two phases: gas and liquid. The gas is removed from the housing and the pressure of the liquid, under centrifugal motion, is sensed and correlated with the mass of the fluid.

3 Claims, 2 Drawing Figures

FLUID MASS SENSOR FOR A ZERO GRAVITY ENVIRONMENT

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 45 U.S.C. 2457).

BACKGROUND OF THE INVENTION

The present invention relates to apparatus and methods for the accurate measurement of the mass of a fluid. In particular this invention pertains to accurate real time mass measurement of fluids at remote locations.

The invention is particularly directed to the real time measurement of the mass of urine discharged by astronauts. It is also useful in the separation and determination of the mass of a liquid mixed with a gas immediately at the time of separation.

In the past few years man has made great strides in exploring outer space. The NASA space program has been characterized by continuous and sometimes spectacular advances. Of course, in making advances in such a program, many problems have been encountered.

One such problem in space travel is the ability to accurately measure and keep bio-medical data on each astronaut to make sure he is in good health. It has been observed that the mass of urine discharged during each micturition of an astronaut is significant as a good diagnostic indicator of whether an astronaut is having some biological malfunction. Thus, it has been found to be important to have an accurate measure of the mass of urinary discharges each time an astronaut urinates.

Another such problem is how to make astronauts as comfortable as possible on long space trips. One way to keep astronauts comfortable is to make the normal body functions of eating and excreting as earth-like as possible. The currently used roll-on cuff for urination in space leaves much to be desired in making the astronaut feel comfortable and earth-like in his environment.

The problem of accurate measurement is further compounded by the necessity of providing a way to accurately measure the urine mass of an astronaut in his zero gravity environment. Most scales, as we known them today, are gravity dependent. The lack of gravity in space creates additional problems in that fluid to be collected will not collect and stay in a container while the measurement of its mass is being made.

Prior methods used in the determination of the mass of urine have been post-flight gravimetric determination based on the mass of the fluid being collected, during flight, but this post-flight bio-medical data does not provide the inflight data which is needed to keep real time medical checks on the astronauts.

Another problem associated with post-flight urine analysis is the filling of the containers without the astronauts having to handle the container. In addition, the astronaut has had to wear a roll-on cuff in order to feed urine into a post-flight collection system. In order to solve these problems it is important to find a means whereby the astronaut can automatically fill the device to be used in measuring the mass of the urine and also to provide the astronaut with a means of collecting wherein the discharge of urine can be more earth-like. Further, as the space hardware designers have begun to develop pneumatic collection systems for urine and fluids, it has become important that the device developed for the measurement of the mass of the urine also be compatible with a pneumatic collection, and yet not sacrifice the accuracy of the measurement of the mass of an astronaut's urine.

SUMMARY OF THE INVENTION

In the present invention, apparatus and methods are provided for accurate measurement of a fluid mass in real time. Further, this invention is compatible with a pneumatic fluid collection apparatus to be used in zero gravity. To these ends the present invention provides a collection system for fluid which is not dependent on gravity for collection or for accurate determination of the fluid mass.

The invention provides an air transport or draft of gas to draw fluids into an inlet of a housing of the invention because there is no gravity to do so in space. After the fluids are drawn into the housing, they are separated into their respective gas or liquid phases by using a multibladed rotor which imparts centrifugal motion to the fluid in the housing and creates a rotating fluid vortex against the inside of the housing. The transport air or gas phase is driven out and a liquid pressure is generated on the inside of the housing. A pressure sensitive transducer is connected to the inside of the housing wall to sense the pressure of the rotation fluid vortex and to correlate it into accurate mass measurements. This operation can occur as an astronaut urinates thus providing timely data on the mass of urine discharged by each astronaut.

This particular invention is perfectly compatible with other pneumatic type collection systems and frees the astronaut because he does not have to handle any urine collection hardware. Also as the urine mass is automatically determined and then dumped into a disposal system, after the mass reading is made, the astronauts do not have to perform any work functions such as mass determination. Also as the accuracy of the liquid mass determination of this invention is excellent, it provides the necessary data for the bio-medical analysis and monitoring of the astronauts.

Another feature of this invention relates to providing the astronaut as earth-like an environment as possible by using the pneumatic system to collect the urine. This eliminates the need for use of the roll-on cuff which has been used in the past.

DRAWINGS

DESCRIPTION OF THE PREFERRED EMBODIMENT

Figure 1:
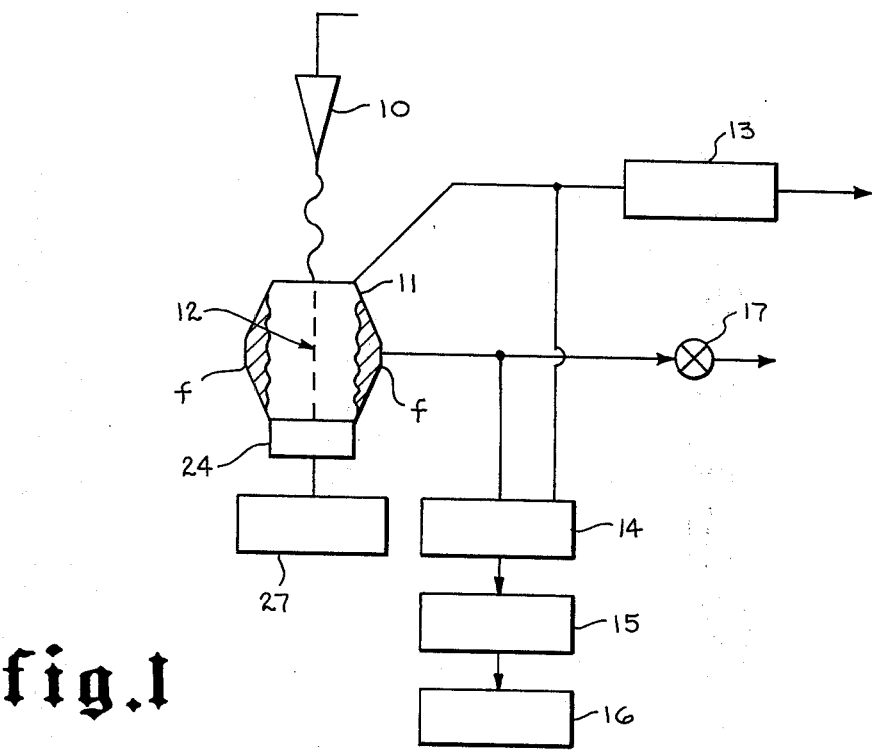
FIG. 1 is a function diagram of the method of operation of this invention.

FIG. 1 is a general diagramatic view of the general features and operation of the apparatus of this invention. In FIG. 1 the apparatus of this invention has provided a urinal into which an astronaut can urinate. Under zero gravity the urinal 10 is fluidly connected through a housing 11 to a draft blower 13 which draws a draft of cabin air into the urinal 10 and thus feeds the urine and cabin air into the housing 11.

As the cabin air and urine are fed into the housing 11, a multi-bladed rotary impeller 12 creates a centrifugal rotating vortex of urine and cabin air, indicated generally in FIG. 1 at f, against the wall of the housing 11. This rotating vortex of urine and cabin air creates the centrifugal forces necessary to separate the urine and cabin air and to hold the urine against the wall of the housing 11 by centrifugal force, while the separated cabin air is drawn out of the housing 11 by the draft blower 13 and discharged.

While the urine is held against the walls of the housing 11 by centrifugal force and after completion of urination by the astronaut, a pressure-sensitive transducer 14 connected to the wall of the housing 11 senses the centrifugal pressure created by the mass of the urine as it is rotated at a constant impeller speed. The pressure sensitive transducer 14 then transmits a signal to a scaler 15 which amplifies the pressure signal transmitted by the pressure sensitive transducer 14 to determine the mass of the urine for a given speed of rotation of the impeller 12. In the more general case, with the impeller speed uncontrolled, the scaler would correlate upon spin with pressure signal to determine mass. A resultant signal from the scaler 15 is then transmitted to a read-out indicator 16 which indicates the mass of the urine collected.

After the mass of the urine has been determined, the astronaut activates a dump valve 17 which discharges the urine from inside the housing 11 into a disposal system, not shown, for treatment or storage.

Figure 2:
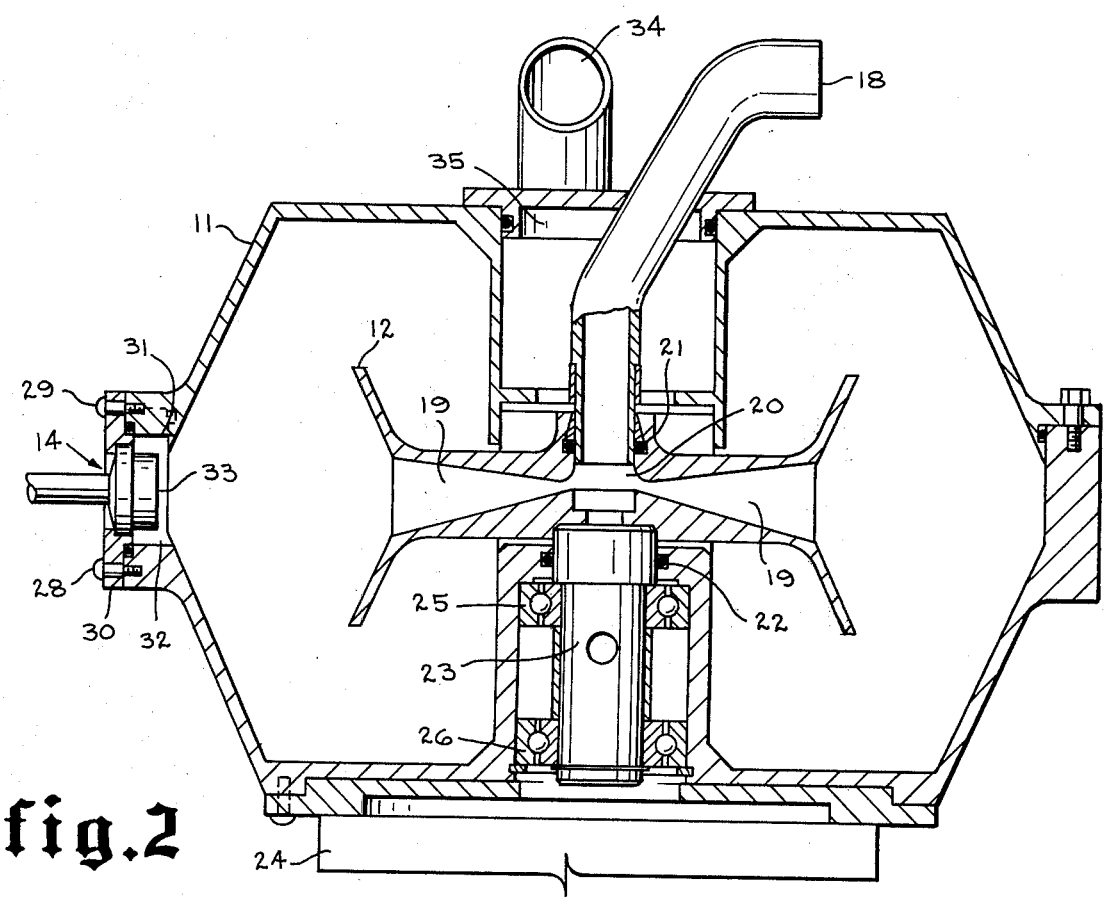
FIG. 2 is an elevation in cross-section of the apparatus of this invention.

Referring to FIG. 2 in the illustrated embodiment, the principal apparatus of the invention includes a cylindrical housing 11 with an inlet 18 leading inside the housing 11 for the introduction of fluid therein. The housing 11 also has mounted at its center a multi-bladed rotary impeller 12 which has flowways 19 therethrough and is in fluid communication with a hollow hub 20 of the multi-bladed rotary impeller 12. A dynamic seal is formed at the union of the inlet 18 and the hub 20 by a ring seal 21. An additional ring seal 22 is fitted around a drive shaft 23 which is connected to a motor 24 at one end and connected to the multi-bladed impeller 12 at the other end for rotation of the multi-bladed impeller 12.

Intermediate the connection point of the motor 24 and the shaft seal 23 are bearings 25 and 26 which allow the shaft 23 connected to the motor 24 to easily turn a constant number of revolutions per minute. To further aid the motor in turning the shaft 23 at a constant number of revolutions per minute, the motor 24 may be connected to a speed controller 27 as shown diagramatically in FIG. 1. It should be understood that a constant and exact speed of rotation is preferable for accurate computation of the mass of the liquid because the centrifugal pressure exerted by the liquid against the housing 11 is a function of the speed of rotation and the mass of the fluid. Consequently, a measure of centrifugal liquid pressure is also a measure of fluid mass.

Mounted on the wall of the housing 11 opposite the multi-bladed rotary impeller 12 by bolts 28 and 29 is the pressure sensitive transducer generally referred to at 14. It should be noted that bolts 28 and 29 pass through an insulation barrier 30 which prevents the transducer from contacting the housing 11. Also, it should be noted that the inside wall of housing 11 is recessed along surfaces 31 and 32 to expose the maximum surface area of a transducer head 33. The purpose for exposing the maximum surface area of the transducer head 33 and for insulation between the wall of housing 11 and the transducer head 33 is to prevent the effect of thermal drift in interpreting the data as read from the transducer 14. It has been found that the fluid entering the housing 11, if it is generally warmer than the walls of the housing 11 and the transducer head 33, creates an artificially high reading, as shown by the data in Table I.

TABLE I

| Time | FLUID TEMPERATURE Meter Reading | |
|---|---|---|
| 0 sec. | 634 | (Sample Injection Complete) |
| 15 | 625 | |
| 30 | 619 | |
| 45 | 616 | |
| 60 | 615 | |
| 75 | 612 | (2% error) |
| 90 | 610 | |
| 120 | 609 | |
| 150 | 608 | |
| 180 | 607 | |
| 240 | 606 | |
| 300 | 605 | (Water Temperature = 87°) |

The faster the transducer head 33 and fluid become more nearly the same temperature, the faster and more accurate the reading of the mass of the urine present. The tapered faces 31 and 32 and the insulation 30 are designed to prevent heat transfer from the transducer 14 to the outer parts of the wall of the housing 11 and to provide the transducer with the maximum exposure to the warm urine which is collected in the housing 11, thus reducing the time required for the hardware and fluid temperature to equalize.

The housing 11 is also provided with an exhaust manifold 34 which is in communication with an outlet 35 of the housing 11 for the discharge of gases from within the housing 11.

In the operation of this invention, the user actuates the motor 24, the speed controller 27, and a blower 13 which is connected to the outlet 35 and then the user proceeds to urinate into a urinal 10. It should be appreciated that in zero gravity the draft of air by the blower 13 feeds the urine by entrainment into the urinal 10 which is in fluid communication with the inlet 18. The urine is then passed through flowways 19 of the multi-bladed rotary impeller 12 and spun against the wall of housing 11 (as shown in FIG. 1) at points along the wall in line with where the pressure transducer 14 is mounted. As the urine is fed into the housing 11, it is a combined mixture of air and urine, but as rotation is continued, the centrifugal force of the urine presses the urine against the wall of housing 11. The air is displaced by the centrifugal forces of the urine and allowed to escape from inside the housing 11, passing through the outlet 35 for discharge through the manifold 34.

As the user continues to urinate, the device continues to collect the urine along the wall of the housing 11, the multi-bladed rotary impeller 12 setting up a centrifugal rotating vortex of fluid over the pressure sensitive transducer exerting a pressure against the pressure sensitive transducer head 33. It should be understood that the pressure exerted by the fluid in zero gravity is a function of the specific gravity of the urine and the speed of rotation of the impeller, and thus can be correlated in terms of the mass of the fluid.

The pressure sensitive transducer head 33 which is located in the wall of the housing 11 senses a pressure and relays it to a scaler 15 which correlates the pressure relayed into a read-out 16 of the mass of urine collected in housing 11. After the mass of the urine has been determined the user trips the discharge valve 17 which dumps the urine from inside chamber 11 to another chamber not shown, either for storage of treatment.

Although only one preferred embodiment of the invention has been described herein, many other variations will be apparent to those skilled in the art. It is therefore intended that the scope of the invention be limited only by the claims which follow.

I claim:

1. An apparatus for sensing and measuring fluid mass, said apparatus comprising:

housing means having inlet means for receiving a liquid-gas fluid stream into said housing means;

outlet means in said housing means for the dumping of fluid from said housing means;

means for introducing a liquid-gas stream into said housing means through said inlet means;

multi-bladed rotary impeller means within said housing means for imparting centrifugal motion to said fluid to form a liquid vortex within said housing means and to separate said fluid into its gas and liquid phases;

power means connected to said rotary impeller means for effecting rotation thereof;

speed controller means operatively associated with said power means for maintaining the rotary speed of said impeller means at a constant number of revolutions per minute; and pressure sensitive transducer means mounted in said housing for sensing the centrifugal liquid pressure and producing an electrical signal indicative of said pressure and representative of said fluid mass.

2. An apparatus as described in claim 1 wherein said means for introducing a liquid-gas stream into said housing means includes a draft blower means for drawing a liquid-gas fluid mixture into said housing means whereby said apparatus is operative in gravity and zero gravity environments.

3. An apparatus as described in claim 1 wherein said rotary impeller means has a hollow hub in fluid communication with said inlet means and flowways through the blades thereof and in fluid communication with said hub whereby fluid received through said inlet means is dispensed through the blades of the impeller means into said housing means.

* * * * *